United States Patent [19]

Grossberg et al.

[11] 4,219,337
[45] Aug. 26, 1980

[54] ASSAY FOR PROTEINS AND POLYPEPTIDES

[75] Inventors: Sidney E. Grossberg; Joseph J. Sedmak, both of Milwaukee, Wis.

[73] Assignee: The Medical College of Wisconsin, Milwaukee, Wis.

[21] Appl. No.: 900,693

[22] Filed: Apr. 27, 1978

[51] Int. Cl.² .................. G01N 33/16; G01N 21/02
[52] U.S. Cl. .............................. 23/230 B; 252/408; 422/56
[58] Field of Search .................. 23/230 B; 422/55, 56, 422/57, 58; 252/408

[56] References Cited

U.S. PATENT DOCUMENTS

| 2,785,057 | 3/1957 | Schwab et al. | 422/58 |
| 3,980,437 | 9/1976 | Kishimoto et al. | 422/55 |

OTHER PUBLICATIONS

Reisner et al., The Use of Coomassie Brilliant Blue G250 Perchloric Acid Solution for Staining in Electrophoresis and Isoelectric Focusing on Polyacrylamide Gels, Anal. Biochem., vol. 64, pp. 509–516 (1975).

*Primary Examiner*—Joseph Scovronek
*Attorney, Agent, or Firm*—Quarles & Brady

[57] ABSTRACT

An assay for proteins or polypeptides in solution using a reagent of Coomassie Brilliant Blue G250 dye in perchloric or hydrochloric acid. Upon mixture of the acidic reagent with a protein sample, the dye couples with the protein and undergoes a color change, following which the absorbance of the mixture can be measured to provide a quantitative analysis for the protein in the sample; the same procedure may be used for sample solutions containing polypeptides. Proteins and polypeptides with molecular weights above about 2000–3000 may be assayed.

6 Claims, 4 Drawing Figures

ASSAY FOR PROTEINS AND POLYPEPTIDES

BACKGROUND OF THE INVENTION (1) Field.

This invention relates to the art of quantitative measurement of protein or polypeptide in solution.

(2) Prior Art.

A variety of methods are available for quantitating proteins present in solutions.

The Lowry procedure is the most commonly employed assay of protein (1) and measures protein with a phenol reagent after alkaline copper treatment. The assay cannot be used on samples containing less than 5 $\mu$g/ml of protein; compounds such as $K^+$, $Mg^{+2}$, ethylene diamine tetraacetic acid (EDTA), tris or thiol reagents interfere with the assay.

The biuret reaction using sodium hydroxide and copper sulfate (2) is prone to interference by tris, $NH_4^+$ and glycerol and is almost two orders of magnitude less sensitive than the Lowry procedure.

Modifications of the above assays have been proposed (3,4) to obviate some of their problems, but the modifications make the assays more time-consuming and introduce additional manipulations.

Ultrasensitive fluorometric assays using fluorescamine have been reported (5,6) but the proteins must be separated from the large number of low molecular weight substances that interfere with the assays. The Kjeldahl assay (7) measures protein nitrogen but is relatively insensitive and very time consuming.

Methods have been reported for quantitating proteins on electrophoretic strips (8) and polyacrylamide gels (9) by staining the protein with Coomassie Brilliant Blue R250 dye. Reisner et al (10) found that Coomassie Brilliant Blue G250 in dilute perchloric acid exhibited a color change when the dye was bound to protein. Bradford (11) has reported a method for quantitating protein in solution based on the color change of Coomassie Brilliant Blue G250 dye in a reagent consisting of 0.01% G250 dye, 4.7% (w/v) ethanol and 8.5% (w/v) phosphoric acid. He found that the ethanol was essential to remove turbidity by solubility the dye/protein complex. U.S. Pat. No. 4,023,933 to Bradford and Williams, is directed to the same process described in the Bradford article (11) and discloses the use of weak acids having a pKa of 0 to 4, preferably 1 to 2, for use with G250 as an assay reagent with an alcohol added to prevent turbidity. The patent specifically states that "Highly ionized acids such as perchloric acid, hydrochloric acid and sulfuric acid cannot be used in the reagent", c. 2, l. 66. A more sensitive dye-binding assay using Amido Schwarz 10B has been reported by Schaffner and Weissman (12) but it requires acid precipitation and collection of the protein on a membrane filter.

The literature citations for the preceding discussion are:

(1) Lowry, O. H., Rosebrough, N.J., Farr, A. L. and Randall, R. J. (1951) *J. Biol. Chem.* 193, 265.
(2) Mokrasch, L. C. and McGilvery, R. W. (1956) *J. Biol. Chem.* 221, 909.
(3) Bensadoun, A. and Weinstein, D. (1976) *Anal. Biochem.* 70, 241.
(4) Shuster, L. and Schrier, B. K. (1967) *Anal. Biochem.* 19, 280.
(5) Bohen, P., Stein, S. Imai, K. and Udenfriend, S. (1974) *Anal. Biochem.* 58, 559.
(6) Nakamura, H. and Pisano, J. J. (1976) *Archives Biochem. Biophys.* 172, 102.
(7) Wagner, B. C. (1940) *Ind. Eng. Chem.* 12, 771.
(8) Fazekas de St. Groth, S., Webster, R. G., and Datyner, A. (1963) *Biochem. Biophys. Acta.* 71, 377.
(9) Diezel, W., Kopperschlager, G. and Hofmann, E., (1972) *Anal. Biochem.* 48, 617.
(10) Reisner, A. H., Nemes, P. and Bucholtz, C. (1975) *Anal. Biochem.* 64, 509.
(11) Bradford, M. M. (1976) *Anal. Biochem.* 72, 248.
(12) Schaffner, W. and Weissmann, C. (1973) *Anal. Biochem.* 56, 502.

SUMMARY OF THE INVENTION

We have found that Coomassie Brilliant Blue G250 dye can be used for the assay of proteins in solution when employed in an acidic reagent with strongly ionic acids such as perchloric acid or hydrochloric acid; the acid should be present at a concentration of about 2.6 to 3.5% (w/v) in the case of perchloric acid and about 1.2 to 2.4% (w/v) with hydrochloric acid. The Coomassie Brilliant Blue G250 dye should be present at a concentration to provide a degree of color change when combined with a protein-containing sample sufficient to enable accurate photometric measurement of the protein concentration; in general, from about 0.01% to 0.1% by weight of the dye in the acid reagent will be suitable. Polypeptides in solution can be assayed in the same manner.

Some of the principal objects of our invention are to provide a new protein assay method, and reagent for use therein, based upon an acidic reagent containing Coomassie Brilliant Blue G250 dye and a strongly ionized acid; to provide a reagent and assay method as defined which employs an acid having a pKa of −3 or less, particularly perchloric acid or hydrochloric acid; to provide a simple, rapid protein assay; to provide a sensitive assay capable of detecting less than 1 $\mu$g of protein; to provide an assay suitable for measuring both large and small volume samples; to provide a reagent for protein assay using Coomassie Brilliant Blue G250 dye which does not require an alcohol, such as ethanol, to prevent turbidity; and to provide a polypeptide assay having the foregoing features.

DESCRIPTION OF THE DRAWINGS

The following description is made in reference to the accompanying drawings, wherein.

DESCRIPTION OF THE PREFERRED EMBODIMENTS

Figure 1:
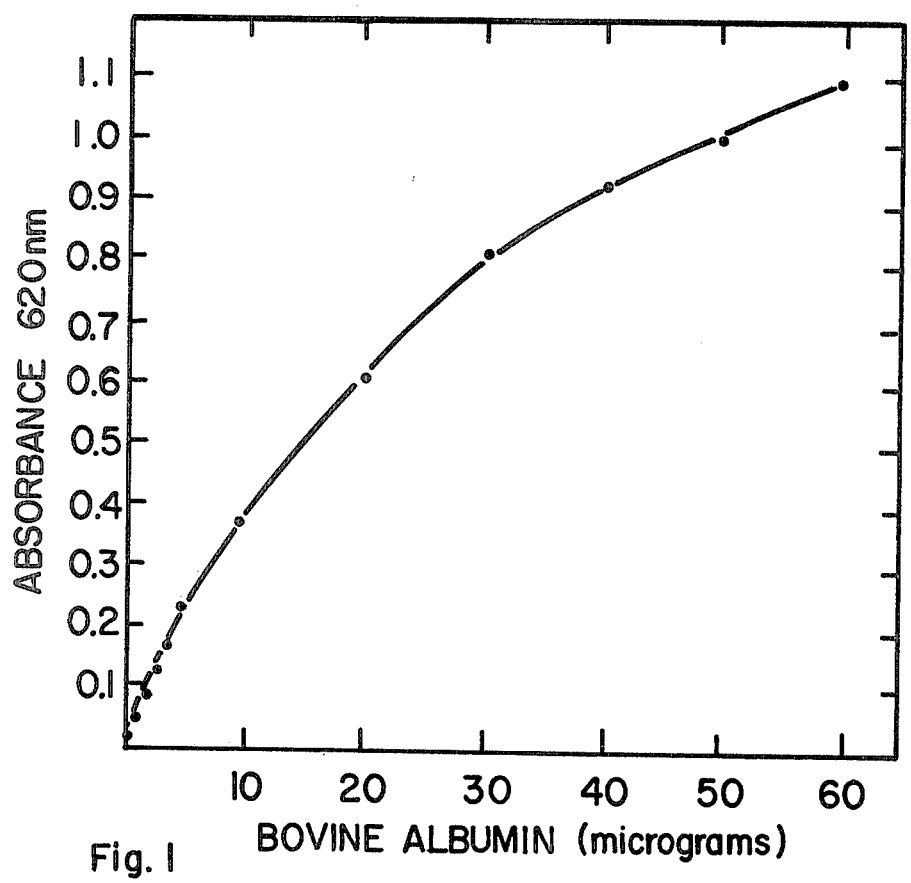
FIG. 1 is a dose-response curve showing the absorbance of bovine plasma albumin (BPA) when determined in accordance with an assay of the present invention.

Our present invention employs an acidic reagent comprising a solution of Coomassie Brilliant Blue G250 dye (G250) and perchloric acid (PCA) or hydrochloric acid (HCl). The PCA is to be present at a concentration of about 2.6 to 3.5% (w/v) when used as the acid in the reagent, and the HCl at a concentration of about 1.2 to 2.4% when it is used as the acid in the reagent. The concentration of G250, a crystalline solid, in the reagent is to be high enough to give sufficient color change when the reagent is mixed with a protein sample to allow accurate photometric measurement, and yet not so high that part of the G250 would not dissolve in the solution; the G250 concentration may be from about 0.01% to 0.1% by weight in general, and a concentration of about 0.06% has been found to be suitable for the assay of many proteins.

The acidic reagent as defined above is mixed with a sample containing protein in solution. The protein couples to the G250 dye, and the dye undergoes a color change from a brownish-orange color to an intense blue. The absorbance of the solution is measured to determine the concentration of the protein in the sample.

Our invention is further described in the following examples in which the materials and procedures described in parts (1)-(3) below were employed.

(1) Reagents and proteins. Coomassie Brilliant Blue G250 was obtained from Eastman Kodak Company, Rochester, NY; a few experiments were done with dye from Serva, Heidelberg. Egg white lysozyme and ovalbumin, both twice crystallized, were purchased from Aldrich Chemical Co., Inc. Milwaukee, WI. Bovine plasma albumin (5X crystalline) was obtained from Metrix, Chicago, IL. Horse heart cytochrome c (90–100% pure) and fetuin (Spiro method, 99% pure) were obtained from Grand Island Biological Co., Grand Island, NY. Porcine stomach mucosa pepsin (2,500 units per mg) was purchased from P-L Biochemicals, Milwaukee, WI. Soybean trypsin inhibitor (5X crystallized) was obtained from Nutritional Biochemicals Corp., Cleveland, OH. Crystalline porcine glucagon and port sodium insulin crystals were obtained from Eli Lilly Co., Indianapolis, IN. Bovine pancreatic trypsin inhibitor and peptide T31, a trypsin digestion product of the carboxymethyl derivative of the inhibitor, were obtained from Dr. B. Kassell, The Medical College of Wisconsin, Milwaukee, WI. Hippuryl-L-arginine and the tripeptides glycylglycylglycine and glycylglycylphenylalanine were obtained from Sigma Chemical Co., St. Louis, MO. Calf thymus DNA and RNA were obtained from Worthington Biochemical Corp., Freehold, NJ. Eagle's minimal essential medium (MEM) in Earle's basal salt solution was purchased from Microbiological Associates, Bethesda, MD. Eagle's MEM in Hanks' basal salt solution (HBSS) was prepared by the additional of MEM essential amino acids and MEM vitamin mixture (obtained from Microbiological Associates) to Hanks' salt solution. Human serum albumin and bovine serum albumin were Milwaukee County General Hospital standards (the BSA was calibrated against the standard supplied by the National Bureau of Standards), and the human urine and human spinal fluid were clinical samples from Milwaukee County General Hospital, all obtained from Dr. B. Doumas, the Medical College of Wisconsin. The fetal calf serum was from Gibco, Grand Island, NY. Antifoam B was obtained from Dow Corning Corp., Midland, MI. All other chemicals were reagent grade or better.

(2) Protein assay–the "standard assay." Except when specified differently in a particular example, the G250 dye was prepared as a 0.06% solution in either 3% PCA (w/v) (0.3 M) or 2.2% HCl (w/v) (0.6 N) and filtered through Whatman No. 1 filter paper to remove any undissolved material. Some batches of dye were a deeper orange than others; if necessary, stock solutions may be diluted with the PCA or HCl solutions to give absorbance of 1.3–1.5 at 465 nm, the absorbance maximum for the leuko form of the dye. These reagents can be stored indefinitely (at least 1 year) at room temperature in a closed container. The proteins were prepared in unbuffered saline. The assay consisted of adding 0.5 ml of the reagent to 0.5 ml of protein solution, mixing immediately and determining the absorbance at 620 nm with a Gilford Model 240 spectrophotometer against a 1:1 mixture of saline and G250. The absorbance maximum for the protein-dye complex may vary somewhat with the batch of dye and should be verified to determine the best wavelength for the assay. Protein concentrations were verified by calculations based upon the molar extinction of the proteins at 280 nm. The standard assay is adaptable to smaller or larger volumes provides that appropriate volumes of the reagent and protein solutions are mixed.

(3) Protein assay–microassay. A reagent was prepared as a 0.06% solution of G250 in 1.9% PCA (w/v) and filtered as above. To 25 $\mu$l of protein solution placed in a well of a disposo-tray (Linbro Chemical Co., Inc., New Haven, CT, model RB-96W), 0.5 ml of the reagent was added, the tray shaken gently, and the absorbance at 620 nm determined as described in (2) above. The microassay can use anywhere from 1 to 50 $\mu$l of protein preparation and the volume of reagent can be increased in order to decrease the sensitivity for use with concentrated protein preparations such as serum.

Example 1

Using the procedure of part (2) above, bovine plasma albumin (BPA) was assayed in accordance with the present invention using both the G250-PCA reagent and the G250HCl reagent.

Figure 2:
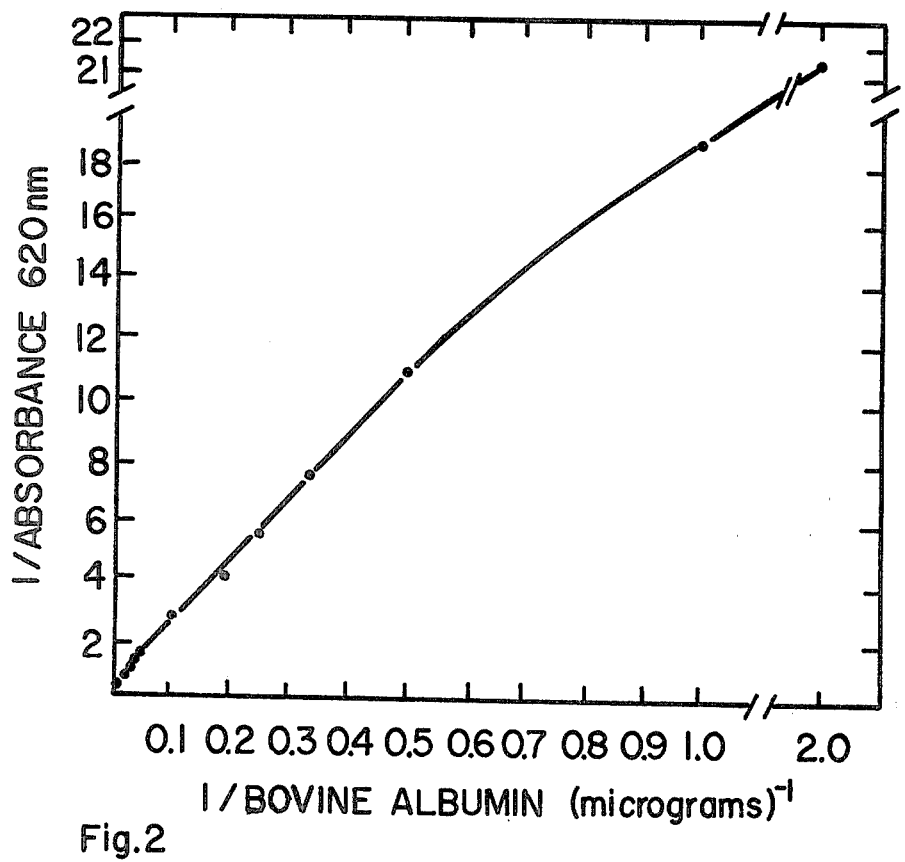
FIG. 2 is a dose-response curve showing the same results in FIG. 1 plotted as the reciprocal of absorbance against the reciprocal of BPA concentration.

The dose-response curve correlating the absorbance measured at 620 nm of the resultant mixture with the amount of BPA is shown in FIG. 1 for the G250-PCA reagent. The curve is nonlinear as is also the case for the Lowry assay. However, as for the Lowry assay [see Cookley at al (1978) Anal. Biochem., 85, 90], when the reciprocal of absorbance at 620 nm is plotted against the reciprocal of the BPA concentration, a linear relationship is obtained throughout a useful range of BPA concentrations; this is illustrated in FIG. 2, from which it will be noted that the curve is linear from about 2 $\mu$g (or 0.5 $\mu$g$^{-1}$ expressed as the reciprocal) to 60 $\mu$g (or 0.0167 $\mu$g$^{-1}$ expressed as the reciprocal) of BPA in the assay sample. A linear dose-response curve also may be obtained by plotting the ratio of the absorbance at 620/465 nm as read against saline with respect to protein concentration after the absorbance ratio of 1:1 G250-PCA- Saline mixture is subtracted from the values.

Figure 3:
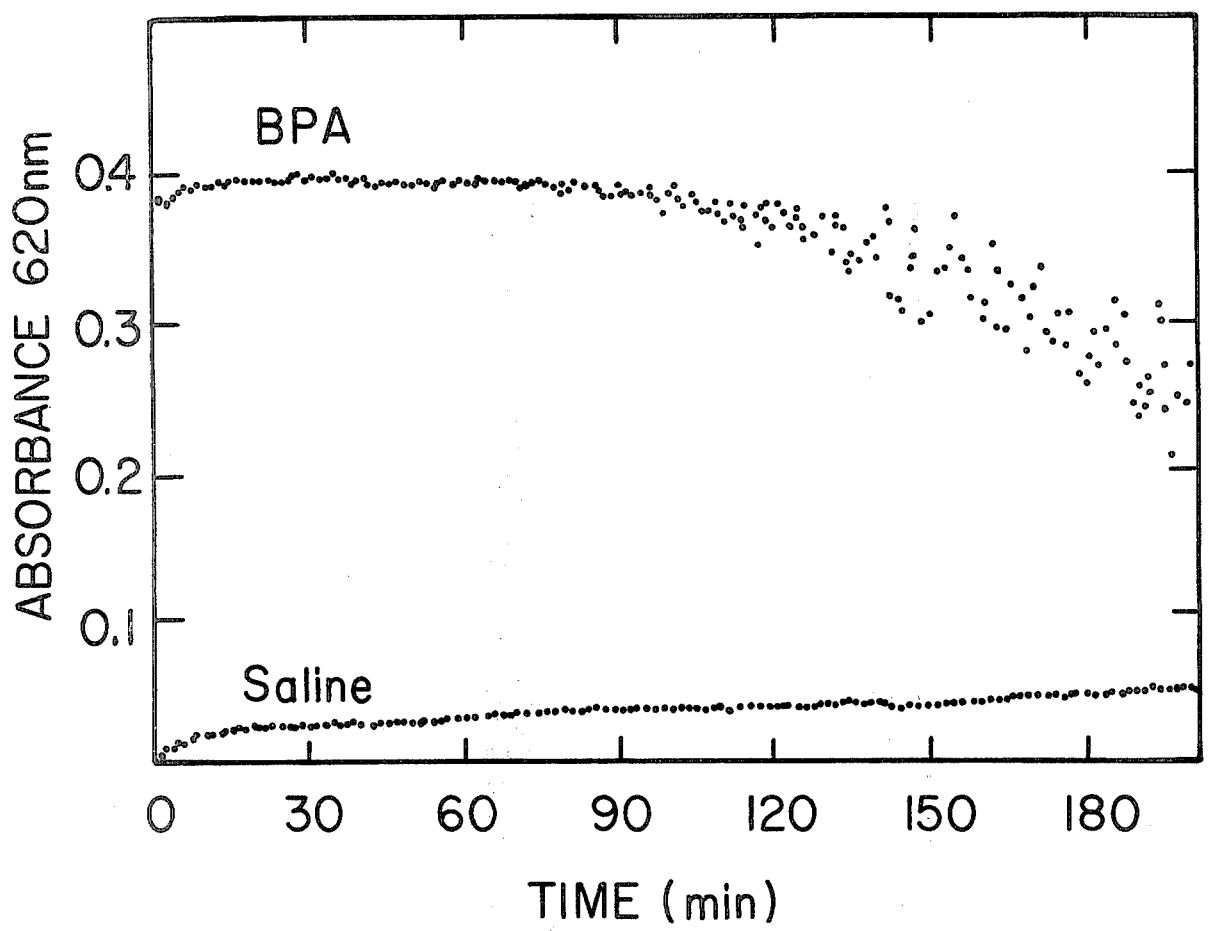
FIG. 3 illustrates the variation in absorbance with time of a BPA sample assayed in accordance with the present invention.

It was noted that the blue color obtained with the G250-PCA assay of BPA was stable for 60–90 minutes at room temperature. FIG. 3 illustrates the variation in the absorbance of samples containing 10 $\mu$g of BPA with time, absorbance again being measured at 620 nm. The color obtained by use of the G250-HCl reagent was stable for 3 to 4 hours.

Example 2

Both the standard assay and the microassay can be used with a range of dye concentration from 0.01 to 0.1% in the reagent. In the microassay 5 μg of bovine albumin had 620 nm absorbance values of 0.520, 0.446, 0.242, and 0.162 at 0.1, 0.06, 0.02 and 0.01% dye concentrations, by weight, respectively. At concentrations greater than 0.1% of dye the absorbance value was essentially the same as at 0.1%, and at concentrations lower than 0.01% the protein dose-response curve was too shallow to be useful.

Example 3

The standard assay can be used over a range of PCA concentrations from 2.6 to 3.5% (w/v). At lower concentrations than 2.6% the G250 dye converts to its colored form when an equal volume of saline is added. At greater than 3.5% concentrations of PCA the proteins become insoluble after a few minutes making it necessary to perform the assay very rapidly. The standard assay of 50 μg of BPA gave absorbances at 620 nm of 1.122, 1.129 and 1.006 at 3.5, 3 and 2.6% concentrations, respectively, of PCA indicating that over this concentration range comparable results are obtained for BPA.

Example 4

The standard assay can also be used over a range of 1.2 to 2.4% (w/v) HCl but like the situation with PCA, at HCl concentrations lower than 1.2% the dye converts to the leuko form even when saline is mixed with the reagent and at higher than 2.4% HCl the protein rapidly becomes insoluble. The absorbance value at 620 nm of 50 μg of BPA was somewhat lower at 1.2 than 2.2% HCl (0.695 versus 0.989).

Examples 5-17

Other proteins were assayed using the procedure of part (2) above. Fetuin (Ex. 5), ovalbumin (Ex. 6), soybean trypsin inhibitor (Ex. 8), lysozyme (Ex. 9), and cytochrome c (Ex. 10) provided dose-response curves parallel to that of BPA (FIG. 1), although the absorbance varied with the individual protein. Polypeptides as small as glucagon (Exs. 11-13) reacted with the reagent and may be analyzed with the present assay. Pepsin (Ex. 7) had a markedly lower absorbance than the other proteins, probably because of its low content of basic amino acids. Oligopeptides (Ex. 14-17) did not react with the reagent; hence, the assay is believed to be useful for the detection of proteins or polypeptides with a molecular weight above about 2,000-3,000.

Absorbance values for 10 μg of the proteins and polypeptides of Exs. 5-17 are tabulated below in Table A. As noted in Table A, the ratio of absorbance obtained with the G250-PCA reagent to that obtained with the G250-HCl reagent is about 1, except for Examples 8 and 11.

TABLE A

| Example | Protein | Molecular weight | Absorbance at 620 nm G250-PCA | Absorbance at 620 nm G250-HCl | Absorbance ratio at 620 nm PCA/HCl |
|---|---|---|---|---|---|
| 1 | Bovine plasma albumin | 67,000 | 0.429 | 0.449 | 0.995 |
| 5 | Fetuin | 46,300 | 0.349 | 0.253 | 1.379 |
| 6 | Ovalbumin | 43,500 | 0.357 | 0.345 | 1.034 |
| 7 | Pepsin | 32,700 | 0.163 | 0.119 | 1.369 |
| 8 | Soybean trypsin inhibitor | 20,095 | 0.350 | 0.092 | 3.804 |
| 9 | Lysozyme | 14,314 | 0.348 | 0.241 | 1.443 |
| 10 | Cytochrome c | 11,702 | 0.465 | 0.531 | 0.876 |
| 11 | Pancreatic trypsin inhibitor | 6,512 | 0.478 | 0.028 | 17.050 |
| 12 | Insulin | 5,700 | 0.437 | 0.358 | 1.218 |
| 13 | Glucagon | 3,483 | 0.469 | 0.309 | 1.521 |
| 14 | T31[a] | 1,839 | 0.000 | 0.000 | — |
| 15 | Hippuryl-arginine | 354 | 0.000 | 0.000 | — |
| 16 | Glycylglycylphenylalanine | 279 | 0.000 | 0.000 | — |
| 17 | Glycylglycylglycine | 189 | 0.000 | 0.000 | — |

[a] A peptide produce of trypsin digestion of the carboxymethyl derivative of bovine pancreatic trypsin inhibitor.

It is advantageous to use a microassay for the assay of small volume samples, i.e. those of 1 to 50 μl, such as solutions having protein concentrations greater than 100 μg/ml or precious samples of small volume. Examples 18-21 illustrate the use of microassay procedures of the present invention.

Example 18

Figure 4:
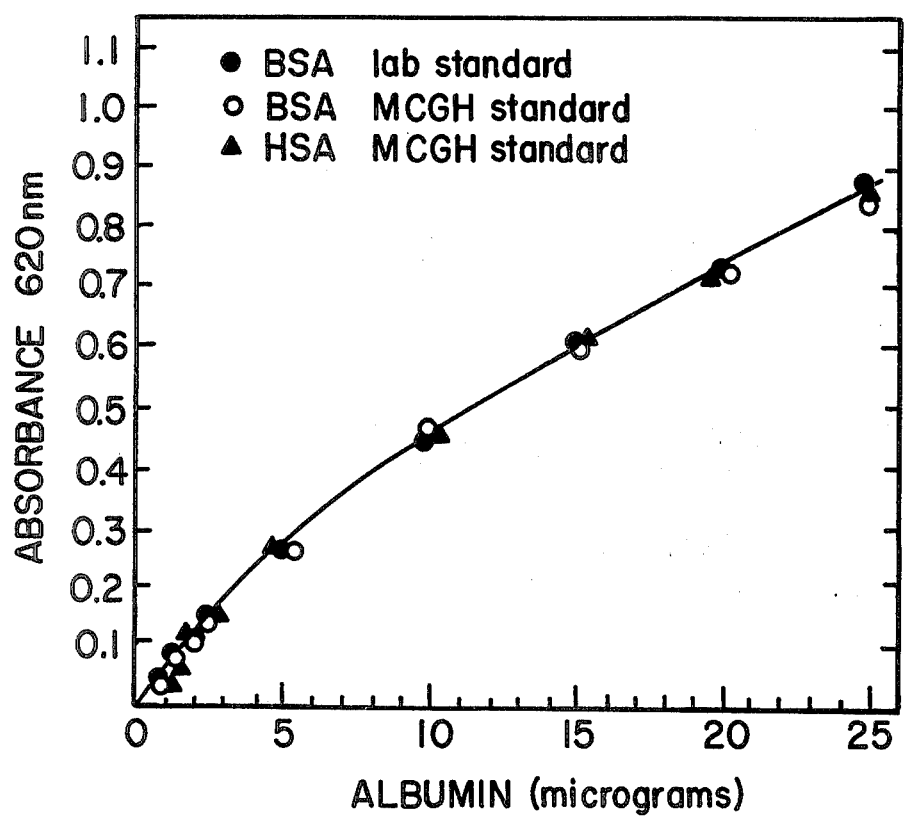
FIG. 4 shows dose-response curves of several proteins determined in accordance with a microassay of the present invention.

The microassay described above under part (3) was used to assay 25 μl samples of BPA prepared in our laboratory at various concentrations using 0.5 ml of a G250-PCA reagent of 0.06% in 1.9% PCA (w/v). FIG. 4 illustrates the dose-response curve with the microassay, each point on the curve being the means of four replicate determinations. It has been found that the microassay can detect less than 1 μg of BPA.

Human serum albumin (HSA) and bovine serum albumin (BSA) standard solutions from Milwaukee County General Hospital (MCGH) also were assayed using the same microassay procedure. Their respective dose-response curves are also shown in FIG. 4. All three preparations gave essentially identical absorbance readings at all protein concentrations tested.

It should be noted that linear dose-response curves for the microassay can be obtained either by use of a double reciprocal curve of the same type as FIG. 2 or by plotting $A_{620}/A_{465}$ ratios, as with the standard assay of part (2) above.

Example 19

The protein content of a serum sample (bovine) was determined to be 30.0 mg per ml by both the microassay of part (3) and the Lowry assay, suggesting that the G250 assay can also be used to determine the protein content of human serum or plasma.

Example 20

The protein content of 16 of 20 human urine specimens obtained from Milwaukee County General Hospital (MCGH) measured by the microassay of part (3) were within 83-103% of the values reported by the MCGH laboratory using the conventional turbidometric acid with trichloroacetic acid. Three of the other values were within 69–76% of the turbidometric acid and the fourth was only 60%.

When 25 μl of urine was used in the assay some of the pathological samples with high protein contents were diluted with saline to give a usable absorbance reading. However by decreasing the sample to 5 μl and increasing the dye reagent to 3.0 ml the need for diluting the pathological specimens was eliminated.

Example 21

The protein contents of 9 of 9 human spinal fluid specimens measured by the microassay of part (3) were essentially identical to the values obtained by the MCGH laboratory with the turbidometric assay. For the spinal fluids no dilutions of the samples were required for the 25 μl microassay suggesting the microassay as described earlier is amenable to automation for detection of spinal fluid protein content.

Example 22

Test devices may be made according to the present invention which can be dipped into a sample solution, or to which a sample solution can be applied, in order to obtain a semi-quantitative analysis of the protein or polypeptide in the sample. The test devices are to include an indicator portion which contains a dried reagent of the types described previously, the indicator portion being of a suitable carrier material such as paper or a suitable coating which can absorb and retain dried reagent. The entire test device can be an indicator portion, such as a strip of paper impregnated with dried reagent; also, part of the test device can be an indicator portion and the balance comprising a material such as plastic or paper which is free of the reagent and can be used as a handle or identification part of the device.

A solution of 0.06% G250 in 1.9% PCA was applied to a paper carrier material and dried. 50 μl of a saline solution containing 2,000 μg/ml of BPA was applied to the impregnated paper; a bright blue color developed and remained after the paper dried. A semi-quantitative determination of the protein in the sample solution is made by comparing the intensity of the color formed on the test device to a color standard showing the various colors obtained at different concentrations of the protein or polypeptide under analysis.

Because protein precipitation is not a problem with a test device of this example, the concentration of PCA or HCl in the reagent can exceed the ranges for these acids in the reagents described previously with respect to the standard assay and the microassay.

Another system for practicing the present assay is to saturate a strip of suitable paper with PCA or HCl, dip the saturated paper first into a protein solution and then into a G250-PCA or G250-HCl reagent to produce a color change on the paper. Under this procedure, using a 3.5% (w/v) PCA solution for initially saturating a strip of paper and a solution of 0.06% G250 in 3.5% PCA as the final reagent after the saturated paper was dipped into the protein sample solution, it was found that as little as 200 μg/ml BPA produced a readily detectable color. The color on the paper can be compared to a color standard to obtain a semi-quantitative measurement of the protein concentration of the sample solution.

As described previously, the assay of the present invention uses a novel reagent consisting of Coomassie Brilliant Blue G250 dye in an aqueous acidic solution of perchloric acid (HClO$_4$) or hydrochloric acid (HCl).

The G250 dye is obtained as a crystalline solid and has the following structure:

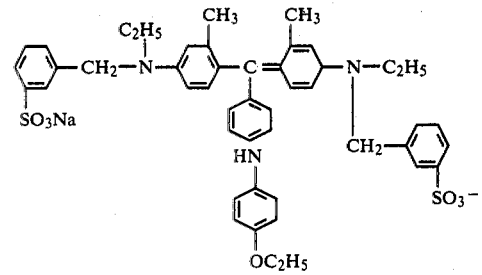

In general, the reagent is to contain from about 0.01 to 0.10%, on a weight basis, of the G250 dye. Concentrations above this range do not appreciably increase the amount of the dye in solution and concentrations below this range usually do not provide a sufficient degree of color change to enable accurate photometric measurements.

The perchloric acid (PCA) and hydrochloric acid (HCl) for use in the present reagents are each strongly ionic acids and have a pKa of −8 and −3 respectively. The PCA is to be at a cocentration of about 2.6 to 3.5% (w/v) and the HCl at a concentration of about 1.2 to 2.4% (w/v). At concentrations lower than these, the G250 dye converted to the colored form when an equal volume of saline was added, even in the absence of protein. At 4% (w/v) or greater concentrations of these two acids, proteins soon became insoluble. Other strong acids, such as sulfuric and nitric acids, at comparable hydrogen ion concentrations were unusable: the G250 dye converted to the leuko form when saline alone was added, and at higher hydrogen ion concentration the dye failed to convert to the blue form in the presence of protein. The use of weak acids (with Ka<1), such as acetic, formic, and iso-butyric acids, was not considered practical since high concentrations were needed to give the pH necessary for maintaining the G250 dye in its leuko form. While either PCA or HCl may be used, PCA is preferred because of the greater variability in absorbance with various proteins when HCl is used, as noted in Table A above.

In accordance with the present assay, the foregoing acidic reagent is mixed with a protein or polypeptide sample solution, the G250 of the reagent couples with the protein or polypeptide of the sample and undergoes a color change to a blue color, and the colored solution is read photometrically to determine the concentration of the protein or polypeptide in the sample. The ratio of the volume of reagent to the volume of protein or polypeptide sample can be varied as long as the final concentration of acid is not so great that protein or polypeptide precipitates nor so dilute that the color fails to develop properly. The colored solutions containing the reagent and the sample have a broad range of absorption; a spectrophotometer may be used to measure absorbancy over a range of about 565 to 644, with readings at the peak absorbance of 620 nm being preferred. The maximum absorbance of the protein-dye complex varied slightly with Coomassie G250 from two different sources, from 595 to 620 nm. The free blue form of the dye at pH 7 in the absence of protein had an absorbance maximum at 580 nm. Addition of protein caused a reduction but not a shift in the absorbance of the leuko form of the dye at 465 nm. The absorbance at 620 nm was a function of the amount of protein or polypeptide. The concentration of a specific sample is ascertained by comparison of its absorbance to a dose-response curve for the protein or polypeptide under investigation, which curves can be made linear over a broad range of concentrations as described above.

The assay may be used for the analysis of both large and small volume samples. Proteins or polypeptides with a molecular weight above about 2,000 to 3,000 may be assayed. The present assay has a high degree of reproducibility. When 10 replicate samples containing 10 μg of bovine plasma albumin were assayed by the "standard assay" with PCA, the standard deviation of the absorbance at 620 nm was only 4% of the mean absorbance. For the "microassay," the standard deviation of absorbance was also less than 5% of the mean.

The assay depends upon the conversion of the dye from the leuko form to an intensely blue color when the dye-anion interacts with the $NH_3^+$ groups of proteins or polypeptides. This interaction appears to be a function of $H^+$ concentration, with dilute PCA and HCl the most effective of the acids tested for use in the assay of proteins in solution. Not all proteins have the same proportion of $NH_3^+$ groups and not all $NH_3^+$ groups react identically to the G250 dye. Thus, the amount of color development in the G250 dye assay varies with the protein used as it does with the Lowry and fluorescamine assays.

The present assay is free of interference from many laboratory solutions. A variety of commonly used protein reagents and buffers were tested for interference with the protein assay. Sucrose, tris, arginine, lysine, antifoam B or glucose and the variety of salts, vitamins, and amino acids present in Eagle's minimal essential medium made up in Earle's or Hanks' salt solution neither produced color nor interfered with this protein assay. Sodium phosphate buffers at 0.1 M produced color in the absence of added protein, probably due to the elevation of pH above that necessary to maintain the G250 dye in its leuko form. Neither DNA nor RNA up to 15 μg interfered with the protein assay; although no color developed with higher amounts, nucleic acid precipitation caused interference. Bovine albumin had a lower absorbance in the presence of 50 μg of DNA, probably the result of coprecipitation of albumin with the DNA, since the centrifuged DNA pellet was blue only when protein was present. Sodium dodecyl sulfate (SDS), urea, phenol, ethylenediaminetetraacetate (EDTA), Tween-80 and sodium sulfate at relatively high concentrations strongly interfere with the assay. When the microassay is used, 12.5 mM EDTA, 0.05 M phenol, 0.6 M urea, 0.1% Triton X-100 and 0.005% SDS did not interfere. Many of these reagents interfere with the Lowry and biuret assays generally used in clinics or laboratories.

Our present assay has numerous important advantages in addition to those previously described. The assay is a simple, rapid and economical assay for proteins or polypeptides. It requires only a single reagent, consisting of a common acid used in dilute solution in combination with a dye, which is stable for over a year. Thirdly, the assay has high sensitivity, being able to detect a tenth of a microgram of protein, e.g. albumin, making it about ten times more sensitive than the Lowry assay.

Further, the assay is versatile, in that it may be employed for the analysis of many different kinds of proteins. This is not the case with a number of other assays which use reagents that react with one or a few proteins.

Another advantage is that the assay does not detect proteins or polypeptides having molecular weights below approximately 2,000-3,000, including amino acids or oligopeptides, thus making it ideal for measuring proteins or polypeptides in mixtures that contain other small molecular weight materials. In contrast, both the Lowry and fluorescamine assays are strongly influenced by amino acids.

The lack of interference by amino acids enables the present assay to be used with crude or natural protein-containing solutions, such as urine, cerebro-spinal fluid, serum, saliva, and other body fluids including secretions, excretions, transudates, exudates, etc. It is possible to determine protein contents of crude preparations without first having to dialyze the sample to eliminate amino acids and small peptides. The amount of protein measured by the present assay was the same (0.6 mg/ml) whether a crude cell extract of human fibroblast cells in Eagle's medium with 2% bovine serum was dialyzed or not. However, the apparent amount of protein measured by the Lowry method was 1.05 mg/ml in the undialyzed crude extract, nearly twice as much as in the dialyzed sample (0.6 mg/ml).

In addition, the assay is useful as a microassay so that only a few microliters of sample need to be employed, and in such assays the volume of reagent to sample can be readily varied. These factors make this assay highly amenable to automated procedures.

Also, the assay can be used with acid-stable proteins, and precious samples can be recovered after the assay has been run.

The assay lends itself to semi-quantitative application; for example, determining the eluates following chromatography or electrophoresis or isoelectric focusing for determining in a spot test the areas of highest protein concentration. In addition the reagent can be employed after impregnation and drying of a suitable indicator portion of a test device, on which a drop of sample can be placed or which can be dipped into a sample and the color read against a color standard.

Our paper published at *Anal. Biochem.* 79, 544 (May 1977) is hereby incorporated by reference. This invention was made during the course of work supported by a USPHS Award (NO1A142520) from the National Institute of Allergy and Infectious Diseases.

We claim:

1. An assay for proteins or polypeptides in solution, comprising the steps of:
   (1) mixing a sample solution containing a protein or polypeptide with an acidic reagent solution comprising Coomassie Brilliant Blue G25 dye and perchloric acid or hydrochloric acid to produce a change of color of the dye, the volume of sample solution and the volume of acidic reagent solution each being such as to provide a perchloric acid concentration in the resultant mixture of about 1.3% to 1.75% (w/v) or a hydrochloric acid concentration in the resultant mixture of about 0.6% to 1.2% (w/v), and
   (2) observing the color of the resultant mixture to determine the concentration of protein or polypeptide in the sample solution.

2. An assay according to claim 1, wherein: the acidic reagent solution contains about 0.01 to 0.10% of Coomassie Brilliant Blue G250 dye by weight.

3. An assay for proteins or polypeptides in solution, comprising the steps of:
   (1) saturating a paper element with an acidic solution comprising about 2.6% to 3.5% (w/v) perchloric acid or about 1.2% to 2.4% (w/v) hydrochloric acid;
   (2) placing the paper element saturated under step (1) into a sample solution containing a protein or polypeptide, and thereafter removing the paper element from the sample solution;
   (3) placing the paper element from step (2) into an acidic reagent solution comprising Coomassie Brilliant Blue G250 dye and about 2.6% to 3.5% (w/v) perchloric acid or about 1.2% to 2.4% (w/v) hydrochloric acid to produce a change of color of the dye; and
   (4) observing the color change produced on the paper element under step (3).

4. The assay of claim 3 wherein:
   the Coomassie Brilliant Blue G250 dye is present in the acidic reagent solution of step (3) at a concentration of about 0.01 to 0.10% by weight.

5. An assay according to claim 1 or claim 2, wherein:
   approximately equal volumes of sample solution and an acidic reagent solution containing about 2.6% to 3.5% (w/v) perchloric acid or about 1.2% to 2.4% (w/v) hydrochloric acid are mixed together.

6. A microassay according to claim 1 or claim 2, wherein:
   approximately 0.5 ml of acidic reagent solution and from 1 to 50 μl of sample solution are mixed together.

(d) Amend claims 7–9 to read as shown below.

* * * * *

UNITED STATES PATENT AND TRADEMARK OFFICE
CERTIFICATE OF CORRECTION

PATENT NO. : 4,219,337
DATED : August 26, 1980
INVENTOR(S) : Sidney E. Grossberg and Joseph J. Sedmak It is certified that error appears in the above—identified patent and that said Letters Patent is hereby corrected as shown below:

Col. 1, line 43, "solubility" should be -- solubilizing --.

Col. 4, line 21, "provides" should be -- provided --.

Col. 6, line 39, after "0.06", insert -- G250--.

Col. 6, line 41, "means" should be -- mean -- .

Col. 8, line 28, "cocentration" should be -- concentration -- .

Col. 12, line 19, delete "(d) Amend claims 7-9 to read as shown below."

Signed and Sealed this

Second Day of December 1980

[SEAL]

Attest:

SIDNEY A. DIAMOND

Attesting Officer

Commissioner of Patents and Trademarks